United States Patent [19]
Schmid

[11] Patent Number: 5,601,720
[45] Date of Patent: Feb. 11, 1997

[54] CONTROLLING A FERMENTATION PLANT

[76] Inventor: Walter Schmid, Puntenstrasse 5, CH-8152 Opfikon, Switzerland

[21] Appl. No.: 230,340

[22] Filed: Apr. 20, 1994

[30] Foreign Application Priority Data

Apr. 21, 1993 [CH] Switzerland .............. 1197/93

[51] Int. Cl.$^6$ .................................... C02F 3/00
[52] U.S. Cl. ................ 210/612; 71/8; 210/614; 210/621; 210/631
[58] Field of Search .................. 210/603, 609, 210/612, 613, 614, 605, 903, 631, 621; 435/166, 167; 71/10, 8, 14, 23

[56] References Cited

U.S. PATENT DOCUMENTS

| | | | |
|---|---|---|---|
| 4,356,269 | 10/1982 | Thomsen et al. | 210/613 |
| 4,442,006 | 4/1984 | Ishida et al. | 210/614 |
| 4,511,370 | 4/1985 | Hunzicker et al. | 210/613 |
| 4,652,374 | 3/1987 | Cohen | 210/603 |
| 4,897,195 | 1/1990 | Erickson | 210/603 |
| 5,248,602 | 9/1993 | Schmid et al. | 210/613 |
| 5,470,745 | 11/1995 | Beteau et al. | 71/8 |

FOREIGN PATENT DOCUMENTS

| | | |
|---|---|---|
| 0131319 | 1/1985 | European Pat. Off. . |
| 0476217 | 3/1992 | European Pat. Off. . |
| 2535756 | 2/1977 | Germany . |
| 2924387 | 1/1981 | Germany . |
| 158700 | 2/1983 | Germany .............. 210/603 |
| 3228895 | 2/1984 | Germany . |
| 2037731 | 7/1980 | United Kingdom ........ 210/603 |
| 8401363 | 4/1984 | WIPO ............... 435/167 |

Primary Examiner—Joseph W. Drodge
Attorney, Agent, or Firm—Weingarten, Schurgin, Gagnebin & Hayes

[57] ABSTRACT

Controlling a fermentation plant working with a horizontal fermentor which operates per the regenerative flow process is particularly difficult, if there is a high proportion of dry substance. Biogenic decomposition in the fermentor was thus far influenced merely by recycling a portion of the ferment from the outlet to the fermentor entrance. According to the invention, the process of control is enhanced by the measurement of the pH and the dry substance portion at various points in the fermentor and controlling the fermentor on the basis of these measurements in such a way that the measurement data lie within certain established ranges. It is additionally possible, moreover, to adjust the pH and the portion of dry substance in the fermentor by the introduction of press water laden with methanobacteria from the ferment at inoculation points in the fermentor.

10 Claims, 1 Drawing Sheet

CONTROLLING A FERMENTATION PLANT

FIELD OF THE INVENTION

The invention relates to fermentation plants, and more particularly to control of fermentation plants.

BACKGROUND OF THE INVENTION

Two known types of procedures for the fermentation of biogenic wastes are known, namely the widespread, batch-processing method with vertical tanks which are extremely slow but easily controlled, and the less widespread procedure, operating continuously in a regenerative flow with a horizontal fermentor which is however difficult to monitor and control.

In the case of the batch-processing method, one or more standing, vertical fermentors are used. The degree of fineness of the chopped biogenic waste is not of particular importance, but merely exerts an influence upon the duration of fermentation. The biogenically decomposed portions drift in the direction of the fermentor outlet. Only near the outlet are samples taken and the time determined at which a batch is to be discharged and new fresh material added. The problem in this case is not so much control, but rather that the heavier components migrate more quickly and consequently arrive at the outlet still not completely decomposed. This is all the more serious because they frequently contain pathogens not killed as a result of too brief a time in the fermentor.

To counteract this, fermentation plants are being increasingly built today with inclined fermentors. According to the degree of slant, the material will flow correspondingly more slowly. A rapid migration of relatively heavy components is thus largely prevented.

The requirement for all known anaerobic fermentors in fermentation plants is still however a mixture with relatively good capacity to flow in the fermentor, to achieve extensive homogeneity in the fermentor, because there are no possibilities available for making corrections.

The plant disclosed in DE-A 3,228,895 thus works with an inclined fermentor, itself rotatably mounted, which works with a mixture of clearing sludge and garbage. This produces a content with the capacity to flow relatively well, whose throughput rate can be controlled at the outlet side and can in addition be influenced by the angle of slant. The material to be loaded in can be given merely a preliminary check and its pH adjusted by adding lime.

The fermentor disclosed in DE-A 2,535,756, on the other hand, operates with highly fluid material, and a powerful agitator prevents the formation of surface scum. In this case, the entire content is mixed, which is not however problematic because batch processing is used.

But even with vertical fermentors the filling material is kept as fluid as possible to achieve homogeneous conditions in the ferment-or. Thus it is proposed in EP 131,319 that the fermentor be charged each time with one part fresh material and two parts of material which is already decomposed. In DE-A 2,924,387, on the other hand, the fill is chopped until the material is fine enough to be pumped.

Although mention is made of the regenerative flow process in various patents with inclined fermentors, it is really only a quasi regenerative flow process which takes place in spurts.

SUMMARY OF THE INVENTION

The present invention concerns control of a fermentation plant in which biogenic wastes to be fermented, chopped up and preheated, are fed to a fermentor in which biogenic decomposition by methanobacteria takes place, in which case biogenic wastes to be fermented, routed to the entrance to the fermentor, can be additionally inoculated with extensively fermented biogenic wastes enriched with methanobacteria from the outlet of the ferment, and the biogenic wastes are decomposed in the fermentor per the regenerative flow process with controlled blending and the formation of biogas and are finally passed to an anaerobic rotting stage.

The invented process works with a completely horizontal fermentor according to EP-A 476,217, which operates per the true, that is to say, continuous regenerative flow process, and thus exhibits varying conditions over its entire length, from the entrance to the outlet.

The task of the invention is now to declare a method permitting excellent control of such a fermentor in a fermentation plant according to the principal concept of the patent claim, so that absolutely reliable continuous operation is possible.

This goal is achieved with the process according to patent claim 1. The method is based on the knowledge that the fill material varies in the case of true regenerative flow operation and is thus also decomposed to varying degrees, which must permit corresponding corrections as the fill material flows through.

An additional point of departure is the biological knowledge that the pH is directly related to the quantity of available and active methanobacteria, which can be added not only at the entrance.

Because the fermentor content can now no longer be blended in the longitudinal axis, it is not stirred, the material being merely rolled around in stages, without being moved forward, so that there is no blending, but merely a rolling movement promoting the escape of gases from the fill material.

The use of press water serves not only for the regulation of the desired moist atmosphere, but at the same time supplies methano-bacteria. This takes place at various points in the fermentor; it is also possible to influence and thus to control the pH by the addition of methanobacteria.

Particularly the delivery of press water laden with methanobacteria into the transporting and mixing segments of the feed pipe permits the inflowing material, consisting mostly of fresh matter, to be adjusted to the desired pH already at the fermentor entrance, thus making later corrective interventions largely unnecessary.

Because the rate of decomposition is also dependent upon temperature, the press water to be passed in is advantageously preheated to that temperature prevailing at the point of injection.

DESCRIPTION OF THE DRAWINGS

The invention will be more fully understood from the following detailed description taken in conjunction with the accompanying drawing in which.

DETAILED DESCRIPTION OF THE INVENTION

Figure 1:
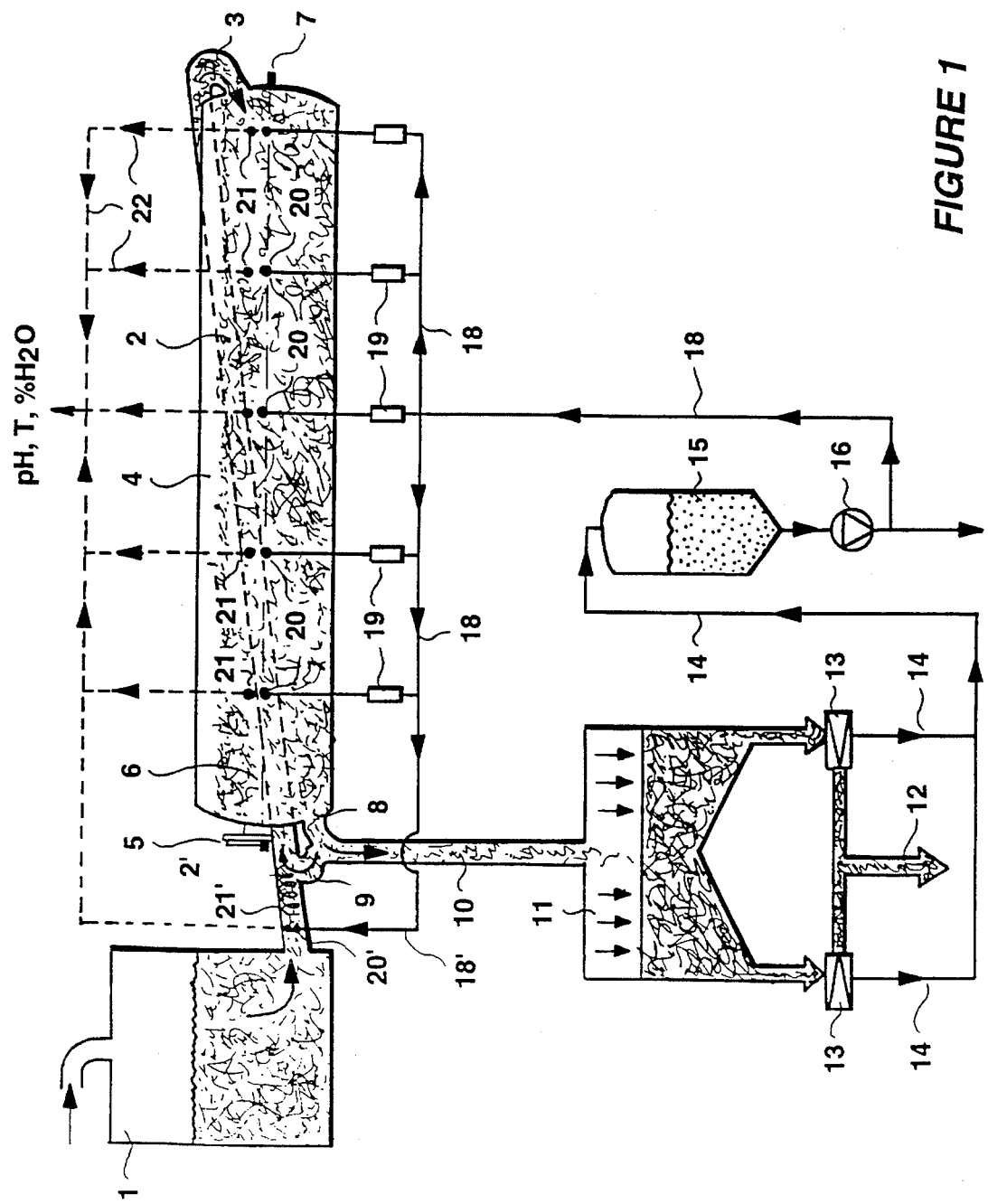
FIG. 1 is a schematic drawing of an embodiment of the invention.

Referring to FIG. 1, the delivered biogenic wastes are separately collected household garbage, garden refuse, as well as rubbish from business enterprises with a large portion of wastes of biogenic origin, such as nurseries, vegetable markets, restaurants, etc., and are stored temporarily in a receiving bin (not shown). From there, they pass through sorting and chopping stations (not shown) to arrive finally in a feed tank 1, from which the biogenic material to be fermented is delivered by metering through a feed pipe 2 to the entrance 3 of a heated anaerobic fermentor 4. Acidification takes place in the feed tank, the pH of the fresh material being adjusted to approximately 5–6. This can also be promoted by use of a supplementary hydrolysis unit. A mixing and transporting segment 2' is provided in the feed pipe 2, which operates preferably with a transporting and mixing worm. Several impeller blades, mounted on a central shaft 6, are moved gradually by a drive 5. The central shaft 6 passes through the entire length of the fermentor 4, the bearing for the opposite end being located at 7. The material to be fermented, moving continuously forward in regenerative flow operation due the material pushed in after it at the entrance, reaches the fermentor outlet 8, where already largely decomposed biogenic wastes can be metered into and mixed with fresh material from the feed tank in the feed pipe 2 by means of a feedback coupling 9.

The extensively biologically degraded material is then passed through a pipe 10 to a press 11, where the water is extracted under pressure from the already fermented material. Through a drainpipe 12, the extensively biologically decomposed material finally reaches a tank (not shown) where aerobic rotting takes place. The completely decomposed material will ultimately be marketed as high quality compost.

The liquid components are removed by means of a separation filter 13 at the outlet of the press 11. This liquid component, the press water, is heavily laden with bacteria, primarily methanobacteria. The press water passes through pipes 14 into an press water tank 15. The excess press water is sent to a press water preparation unit (not shown) by means of a pump 16. There, the press water is further decomposed by means of a special anaerobic filter system, with the production of additional biogas.

Another part of the press water reaches various inoculation points 20 of the fermentor 4 over control tubes 18. Near the inoculation points 20 are also measurement points 21. At these locations it is possible to determine the pH, the temperature and the moisture content of the fermentor contents in each region. Via data lines 22 it is possible to send these data to a central evaluation unit.

A further branch 18' of the control tubes 18 extends into the region of the transporting and mixing segment 2' of the feed pipe 2. An inoculation point 20' and a measurement point 21' are arranged there, too. This allows the fresh material to be charged with bacteria already by means of the press water and adjusted to an optimal pH. The narrower the limits of pH already at the entrance to the fermentor 4, the fewer the control interventions required subsequently. The measurement data from the mixing and transport segment 2' are likewise sent over the data line 22 to the central evaluation unit.

The course of the invented process will now be described below. The composition of the fresh material in the feed tank 1, consisting of biogenic wastes, already separated from materials which are not biologically degradable, like glass, metal and plastics, and already chopped, cannot be influenced. It arrives through the feed pipe 2 at the entrance 3 of the anaerobic fermentor 4. The fresh material is preheated already in the feed pipe 2 to a temperature particularly favorable to the growth of methanobacteria, preferably to temperatures between 30° and 60° C. To enrich the fresh material with material already enriched with bacteria, already extensively biologically degraded material from the outlet 8 of the fermentor 4 is inoculated in an obvious manner into the feed pipe 2 by means of a feedback coupling 9. This material at the entrance to the fermentor 4 is relatively dry and consequently with a high dry substance content and relatively coarse, with particle magnitudes of up to approximately 10 cm. The material in the fermentor does not of course flow by itself. It can merely be forced through the fermentor in true regenerative flow operation by the material pushed in after it. The pH, the temperature and the moisture content are determined at a first monitoring point. 21 at the entrance to the fermentor 4. Typical readings at this location are pH 7.2 to 6.5, thus in the neutral to slightly acid range. The pH is preferably adjusted to about 7. At the fermentor outlet the pH is about 8.4 to 7.5, that is to say, in the basic range, preferably at approximately pH 8.

For adjustment of the pH there are various means available. Near the entrance, the pH can be appropriately adjusted by way of the mixing ratio of fresh material from the feed tank 1 to already extensively decomposed putrefied matter from the anaerobic fermentor 4 via the feedback coupling 9. It is thereby possible to raise the pH by adding a larger quantity of putrefied matter, or to lower it by reducing that quantity.

A further option for influencing the pH is to lower the amount of fresh material added. This prolongs the time spent in the fermentor. The result is that the methanobacteria have more time to propagate, particularly near the nutrient-rich entrance, thus producing a slight increase in pH near the entrance, though the pH will also rise somewhat more sharply at the outlet than with the usual rate of throughput. This method is used, when the moisture content near the entrance already lies in the upper range.

If the proportion of dry matter is high but the pH at the entrance relatively low, there is also in this region the option of introducing bacterially laden press water from the press water tank 5 into the fermentor 4 through the control tube 18. This will increase the density of the methanobacteria and increase the humidity, accelerating the rate of bacterial decomposition.

Increasing the addition of material at the entrance will obviously also increase the rate of throughput everywhere throughout the entire fermentor and in the same way. It is consequently also possible to prevent the pH at the outlet from rising above a desired value by increasing the throughput rate.

It is can usually be assumed that the pH will rise continuously within a permissible range during passage of the material through the fermentor, but deviations can occasionally occur, especially due to the premature dying off of the methanobacteria. This will then lead to a change in the pH. In the invented process, the pH is for that reason determined at several points and corrections implemented directly at the corresponding site. This takes place in turn by the addition of press water through the control tubes 18.

Preferable is the attempt to keep the pH of the charging material, that is to say, the fresh material, or the mixture of fresh material from the feed tank 1 and putrefied matter from the outlet of the ferment already within the narrowest limits possible. This will reduce the number of corrective interventions. Per the invention, press water is consequently introduced already into the transporting and mixing segment 2' of the feed pipe 2. Via the branch 18' of the control tube 18, this reaches the inoculation point 20' right next to the monitoring point 21' A neutralization favorable to the propagation of methanobacteria is scarcely achieved while the fresh material is acid but the press water basic. This could not be achieved by the addition of fresh water, or would require much larger quantities, which in the case of the invention is to be avoided.

Finally, the course of the temperature inside the fermentor 4 is monitored. To prevent the temperature from being impermissibly lowered by control interventions in the form of press water addition, it is desirable to heat the control lines 18 to a temperature at least near that prevailing inside the fermentor by means of a heating element 19. The heating element can be an electric heater or even a heat exchanger. Even the fermentor itself, which is heated by heating lines (not shown), can be warmed in segments. This allows the temperature throughout the charge in the fermentor to be varied to achieve the optimal conditions of growth for the methanobacteria.

Although the production of biogas is an essential task in the case of such a fermentation plant, it will not be further taken up here. The fermentor must obviously be equipped with appropriate outlets for the biogas developed inside the fermentor. The controlled course of pH and temperature, as well as the optimal adjustment of the moisture content, leads to the greatest possible production of biogas, because the living conditions for methanobacteria are optimal. A significant feature of the invented process is also that the material inside the anaerobic fermentor 4 is not mixed by an agitator, as in the known process, but merely turned over slowly in stages. The result is merely that the methane and $CO_2$ gases liberated are better able to escape. This method however prevents the still barely degraded fill from reaching the fermentor outlet.

The atmosphere which is unusually dry for such processes, without a continuous liquid phase in the fermentor, renders the transport of viruses or bacteria via the liquid phase impossible during the brief period from the entrance to the outlet of the fermentor and thus prevents contamination of the arising compost.

A throughput rate of approximately 20 days, astonishingly high for such fermentation plants, is achieved by optimizing the conditions inside the container.

Although the invention has been shown and described with respect to an illustrative embodiment thereof, it should be appreciated that the foregoing and various other changes, omissions and additions in the form and detail thereof may be made without departing from the spirit and scope of the invention as delineated in the claims.

What is claimed is:

1. A method for controlling a fermentation plant, comprising the steps of:

feeding biogenic wastes into the entrance of a fermentor, said fermentor comprising methanobacteria, said methanobacteria decomposing said biogenic wastes to decomposed biogenic wastes, said biogenic wastes having a pH and comprising one or more dry substance components, said decomposition taking place by the regenerative flow method; and passing said decomposed biogenic wastes to an anaerobic rotting stage;

wherein said pH and the value of said one or more dry substance components of said decomposing biogenic wastes are respectively monitored and adjusted at a plurality of points in said fermentor, and wherein the rate of throughput of said biogenic wastes in the fermentor is controlled by monitoring the rate of addition of said biogenic wastes to said entrance of said fermentor and by recycling decomposed biogenic wastes to said fermentor.

2. Process according to claim 1, characterized by the fact that the content of the fermentor is turned over in stages without being moved forward.

3. Process according to claim 1, characterized by the fact that the fermentor is controllably heated in predefined areas.

4. The process of claim 1, further comprising the steps of:

pressing said decomposed biogenic wastes to collect a liquid component;

transferring said decomposed, pressed, biogenic wastes into an aerobic rotting stage;

and adjusting a nominal dry substance value and pH of said wastes in said fermentor by the addition of said liquid component.

5. Process according to claim 4, wherein said fermentor includes a transporting and mixing segment and wherein the pH and the dry substance value are determined in the region of said transporting and mixing segment, said last mentioned respective pH and dry substance value being correspondingly adjusted by addition of a liquid component.

6. Process according to claim 4, characterized by the fact that the liquid component is introduced into the fermentor at a plurality of measurement points.

7. The process of claim 6, wherein measurements are taken at measurement points including include measurement of pH, measurement of moisture content, and measurement of temperature.

8. Process according to claim 4, characterized by the fact that the liquid component is heated before introduction into the fermentor.

9. The process of claim 4, wherein said liquid component is press water laden with methanobacteria.

10. The process of claim 1, wherein said biogenic wastes being fed are inoculated with a portion of said decomposed biogenic wastes.

* * * * *